United States Patent
Lee et al.

(10) Patent No.: US 11,052,026 B2
(45) Date of Patent: Jul. 6, 2021

(54) MULTI-CAPSULE CONTAINING PIGMENT FOR COSMETIC MATERIAL OR FUNCTIONAL COMPONENT, AND METHOD FOR PRODUCING SAME

(71) Applicant: CHEMLAND. CO., LTD., Pyeongtaek-si (KR)

(72) Inventors: Beum Zoo Lee, Seongnam-si (KR); Su Eok Cho, Hwaseong-si (KR); Soon Kyu Jung, Goyang-si (KR); Min Tae Kim, Gunpo-si (KR)

(73) Assignee: CHEMLAND. CO., LTD., Pyeongtaek-si (KR)

( * ) Notice: Subject to any disclaimer, the term of this patent is extended or adjusted under 35 U.S.C. 154(b) by 87 days.

(21) Appl. No.: 16/458,817

(22) Filed: Jul. 1, 2019

(65) Prior Publication Data

US 2019/0321272 A1    Oct. 24, 2019

Related U.S. Application Data

(63) Continuation of application No. PCT/KR2017/014178, filed on Dec. 6, 2017.

(30) Foreign Application Priority Data

Jan. 2, 2017  (KR) .................. 10-2017-0000069

(51) Int. Cl.
*A61K 8/11*   (2006.01)
*A61K 8/29*   (2006.01)
(Continued)

(52) U.S. Cl.
CPC .................. *A61K 8/11* (2013.01); *A61K 8/29* (2013.01); *A61K 8/368* (2013.01); *A61K 8/67* (2013.01);
(Continued)

(58) Field of Classification Search
None
See application file for complete search history.

(56) References Cited

U.S. PATENT DOCUMENTS 6,790,643 B2 * 9/2004 Becker .................... C12N 9/98
                                                    435/177
9,662,283 B2 * 5/2017 Lemoine ................... A61K 8/11
(Continued)

FOREIGN PATENT DOCUMENTS

KR    10-0294792 B1    9/2001
KR    10-0978583 B1    8/2010
(Continued)

OTHER PUBLICATIONS

Notice of Allowance issued by the Korean Intellectual Property Office for corresponding Korean Patent Application No. 10-2017-0000069, dated Sep. 21, 2018, with an English translation.
(Continued)

*Primary Examiner* — Cachet I Proctor
(74) *Attorney, Agent, or Firm* — Myers Wolin, LLC (57) ABSTRACT

The present invention relates to a method for producing a multi-capsule, the method including steps of: (a) preparing a coating solution by mixing purified water, titanium dioxide, mica, a hydrophobic polymer, cellulose gum, and sucrose; and (b) drying the coating solution prepared in step (a) while spraying the coating solution through a spray nozzle of a fluid bed dryer after introducing a spherical seed of a colorant component for a cosmetic; or a starch or sucrose spherical seed coated with a functional component into the fluid bed dryer, a multi-capsule produced by the method, and a cosmetic composition containing the multi-capsule as an active component.

5 Claims, 7 Drawing Sheets

(51) Int. Cl.
  *A61K 8/368* (2006.01)
  *A61K 8/67* (2006.01)
  *A61K 8/73* (2006.01)
  *A61Q 19/00* (2006.01)

(52) U.S. Cl.
  CPC .............. *A61K 8/731* (2013.01); *A61K 8/732* (2013.01); *A61Q 19/007* (2013.01); *A61K 2800/43* (2013.01); *A61K 2800/63* (2013.01); *A61K 2800/65* (2013.01); *A61K 2800/805* (2013.01)

(56) References Cited

U.S. PATENT DOCUMENTS

| | | | | |
|---|---|---|---|---|
| 2006/0172909 | A1* | 8/2006 | Schmiedel | C11D 3/3945 510/267 |
| 2007/0032396 | A1* | 2/2007 | Schmiedel | C11D 3/222 510/302 |
| 2007/0292687 | A1* | 12/2007 | Pommersheim | A61K 9/5073 428/402.2 |
| 2008/0213322 | A1* | 9/2008 | Birman | C09C 3/12 424/401 |
| 2012/0015010 | A1* | 1/2012 | Cummins | C08K 3/22 424/401 |
| 2012/0141584 | A1* | 6/2012 | Chauhan | A61K 9/2866 424/457 |
| 2014/0086861 | A1* | 3/2014 | Goldlum | A61K 8/556 424/63 |
| 2015/0250689 | A1* | 9/2015 | Dardelle | A61Q 15/00 510/130 |
| 2017/0071865 | A1* | 3/2017 | Goldstein | A61K 9/167 |

FOREIGN PATENT DOCUMENTS

| | | | | |
|---|---|---|---|---|
| KR | 10-2013-0047842 | A | | 5/2013 |
| KR | 10-1363757 | B1 | | 2/2014 |
| KR | 10-2016-0015335 | A | | 2/2016 |
| KR | 10-2016-0030215 | A | | 3/2016 |
| KR | 20160030215 | A | * | 3/2016 ............... A61K 8/86 |

OTHER PUBLICATIONS

Written Opinion of the International Searching Authority issued by the Korean Intellectual Property Office for corresponding International Patent Application No. PCT/KR2017/014178 dated Mar. 21, 2018, with an English translation.
International Search Report (ISR) issued by the International Searching Authority issued by the Korean Intellectual Property Office for corresponding International Patent Application No. PCT/KR2017/014178 dated Mar. 21, 2018, with an English translation.

* cited by examiner

MULTI-CAPSULE CONTAINING PIGMENT FOR COSMETIC MATERIAL OR FUNCTIONAL COMPONENT, AND METHOD FOR PRODUCING SAME

CROSS-REFERENCE TO RELATED APPLICATION

This application is a continuation of PCT/KR2017/014178, filed Dec. 6, 2017 and claims priority from Korean Patent Application No. 10-2017-0000069 filed on Jan. 2, 2017 in the Korean Intellectual Property Office, the disclosure of which is incorporated herein by reference in its entirety.

TECHNICAL FIELD

The present invention relates to a method for producing a double- or multi-capsule, in which a material constituting a core is produced and the surface thereof is coated with primary to tertiary coating materials sequentially to form multi-layers of respective different components. An object of the capsule is to prevent decolorization and oxidation of an active component by blocking the internal colorant and functional components from light or oxygen and maximize the effect thereof by preserving the original efficacy until the time when the internal colorant and functional components are used as a cosmetic. Further, although a capsule containing a colorant component for a cosmetic has a white surface, it has a seed with various colors in the inner core part, thereby producing a capsule having an effect in that the capsule has a white color before use as a cosmetic, but when a user uses the cosmetic, a color appears like magic while the capsule is burst by rubbing.

BACKGROUND ART

Cosmetics are classified into various types according to the use site, the purpose of use, the constituent component and shape of a product, or the like, and may be divided into basic cosmetics, makeup cosmetics, body care cosmetics, hair care cosmetics, oral cosmetics, aromatic cosmetics, and the like that are often used daily.

Basic cosmetics may be defined as those cleaning the skin and sufficiently moisturizing the stratum corneum, and are divided into toners, emulsions, serums, creams, and the like. The toner tidies up the skin texture, and the emulsion, called lotion, smoothes the skin, prevents the skin's moisture from evaporating, and improves the spreadability of the cream. The serum is also referred to as an essence, is a highly concentrated cosmetic liquid that maintains skin homeostasis, and prevents dryness and roughness of the skin, and the cream is the last step of the basic care, and an active component of the cream serves to protect the stressed skin healthily.

Cosmetic raw materials containing natural functional components and vitamins are oxidized by oxygen in the air when exposed to air or sunlight, rancidified, and decolorized by ultraviolet rays of sunlight to lose their original functions, so that there is a disadvantage in that they do not fit the purpose of use.

Among cosmetic raw materials, vitamin C is used as a whitening raw material, anthocyanin has an antioxidant effect as a natural raw material taking on a purple tint, and lycopene is utilized as a red carotenoid antioxidant. Xanthophyll is a yellow natural colorant and is utilized as a moisturizing agent because xanthophyll is effective in blocking water evaporation, and chlorophyll has an excellent antioxidant function, and thus is highly effective in suppressing free radicals, so that chlorophyll is utilized as a functional cosmetic.

However, when applied directly to cosmetic formulations, these components are easily decolorized or cause rancidification, thereby resulting in deterioration in the formulation and a change in color, so that these components may not be used directly. Further, among cosmetic raw materials, colored cosmetic colorants are used, and these colorants have a disadvantage in that these colorants may not maintain the inherent white color when applied directly to creams, lotions, and the like.

Korean Patent No. 0294792 discloses a vitamin capsule for a cosmetic and a cosmetic composition including the same, Korean Patent No. 1363757 discloses a method for producing a double capsule for a cosmetic, but these patents are different from a multi-capsule including a colorant or functional component for a cosmetic and a production method thereof.

DISCLOSURE

Technical Problem

The present invention has been contrived in view of the requirements as described above, and in the present invention, a technique for producing a double capsule has been established, in which the inner color may not be distinguished in terms of appearance by putting a colorant into the inside of a capsule and coating the outer side of the capsule with a white material having a color inherent to the cosmetic.

Further, a technique for producing a multi-capsule capable of preserving a functional component until the functional component is used as a cosmetic has been established by putting the functional component into the inside of a capsule, surrounding the capsule with a protective layer, and coating the outermost part of the capsule with a film which prevents moisture permeation in order to prevent deterioration at the time of exposing the functional component to the outside.

Commonly, a technique that allows the efficacy of an original raw material component to be maximized as much as possible has been established by allowing these capsules to be preserved and maintained during the production of a cosmetic and without any deformation or damage to the capsule for a long period of time in the formulation, allowing the desired color of a colorant to be reproduced while the capsule is broken gently at the time of applying the capsule to the skin by a user, and allowing the functional component to be applied to the skin.

In addition, similar capsules in the related art may not overcome disadvantages in that the capsules are not broken easily when applied to the skin, or generate a residue, which reduces the feeling of use at the time of applying the capsule to the skin, and the applied surface becomes dirty due to the residue.

However, a multi-capsule produced by the present invention has overcome these problems because the capsule is broken gently and no residue remains when a cosmetics end-user applies the capsule to the skin by addressing these disadvantages.

Technical Solution

In order to solve the problems, the present invention provides a method for producing a multi-capsule, the method including steps of: (a) preparing a coating solution by mixing purified water, titanium dioxide, mica, a hydrophobic polymer, cellulose gum, and sucrose; and (b) drying the coating solution prepared in step (a) while spraying the coating solution through a spray nozzle of a fluid bed dryer after introducing a spherical seed of a colorant component for a cosmetic; or a starch or sucrose spherical seed coated with a functional component into the fluid bed dryer.

Further, the present invention provides a multi-capsule produced by the method.

In addition, the present invention provides a cosmetic composition containing the multi-capsule as an active component.

Advantageous Effects

1. Provided are a double capsule in which a color is concealed by putting a colorant for a cosmetic into an inside of a core and appropriately blending a white pigment such as titanium dioxide and mica, an adhesive, and a hydrophobic polymer having water resistance to coat the outer side of a colorant seed, and the color of the inside is reproduced like magic while the capsule is broken when a user uses the capsule by applying the capsule to a cosmetic, and a production method thereof.

2. Provided are a multi-capsule which is stable and can preserve and maintain internal components by blending a functional material for a cosmetic, including a starch seed, a sucrose seed, and a white seed as a base to coat an inside of a core, preparing a secondary capsule layer by appropriately blending a white pigment such as titanium dioxide and mica so as to block the outer side of the inside of the core from light and oxygen, an adhesive, and a hydrophobic polymer having water resistance to coat the outer side of the inside of the core again, and finally preparing a tertiary capsule layer in the form of a film on the surface of the capsule from the hydrophobic polymer to prevent moisture permeation in the formulation, and a production method thereof.

Further, an active component can be stably maintained until the time when the capsule is applied to the skin, so that an effect of improving the skin upon use thereof can be maximized. In addition, the multi-capsule produced by the present invention has excellent stability in a cosmetic formulation, and thus can be applied to any formulation such as W/O, O/W, W/S, and S/W.

MODES OF THE INVENTION

In order to accomplish the objects of the present invention, the present invention provides a method for producing a multi-capsule: the method including steps of:

(a) preparing a coating solution by mixing purified water, titanium dioxide, mica, a hydrophobic polymer, cellulose gum, and sucrose; and (b) drying the coating solution prepared in step (a) while spraying the coating solution through a spray nozzle of a fluid bed dryer after introducing a spherical seed of a colorant component for a cosmetic; or a starch or sucrose spherical seed coated with a functional component into the fluid bed dryer.

In the method for producing a multi-capsule of the present invention, the coating solution of step (a) may be prepared preferably by mixing 63 to 69 parts by weight of purified water, 23 to 27 parts by weight of titanium dioxide, 4 to 6 parts by weight of mica, 2.5 to 3.5 parts by weight of a hydrophobic polymer, 0.4 to 0.6 part by weight of cellulose gum, and 0.4 to 0.6 part by weight of sucrose based on 100 parts by weight of the coating solution, and may be prepared more preferably by mixing 66 parts by weight of purified water, 25 parts by weight of titanium dioxide, 5 parts by weight of mica, 3 parts by weight of the hydrophobic polymer, 0.5 part by weight of cellulose gum, and 0.5 part by weight of sucrose based on 100 parts by weight of the coating solution.

Further, in the method for producing a multi-capsule of the present invention, the hydrophobic polymer means a polymer of components having an affinity for oil, and specific examples thereof include one or more selected from the group consisting of polymethyl methacrylate, polyethyl methacrylate, polypropyl methacrylate, trimethylsiloxysilicate, a VP/eicosene copolymer, an acrylate/polytrimethylsiloxymethacrylate copolymer, and an acrylate/stearyl acrylate/dimethicone methacrylate copolymer, and polymethyl methacrylate may be preferably used, but the hydrophobic polymer is not limited thereto.

The method for producing a multi-capsule including a colorant component of the present invention may include steps of: (a) preparing a spherical seed of a colorant component by spray-drying a mixture obtained by mixing a colorant component for a cosmetic selected from the group consisting of iron oxide yellow, iron oxide red, iron oxide black, chromium oxide green, and ammonium manganese phosphate with purified water, titanium oxide, cellulose gum, and sucrose; (b) preparing a coating solution by mixing 66 parts by weight of purified water, 25 parts by weight of titanium dioxide, 5 parts by weight of mica, 3 parts by weight of a hydrophobic polymer, 0.5 part by weight of cellulose gum, and 0.5 part by weight of sucrose based on 100 parts by weight of the coating solution; and (c) drying the coating solution prepared in step (b) while spraying the coating solution through a spray nozzle of a fluid bed dryer after introducing the spherical seed of the colorant component prepared in step (a) into the fluid bed dryer.

In addition, the method for producing a multi-capsule including a functional component of the present invention may more specifically include steps of: (a) producing a core seed by introducing, into a fluid bed dryer, sucrose or a mixture obtained by mixing one or more components selected from the group consisting of corn starch, sucrose, titanium dioxide, and cellulose gum with purified water, and then drying the resulting mixture while spraying the mixture;

(b) preparing a functional component mixture by mixing one or more functional components selected from the group consisting of lycopene, anthocyanin, xanthophyll, chlorophyll, ascorbic acid, and salicylic acid with purified water, corn starch, a hydrophobic polymer, and cellulose gum;

(c) primarily coating the core seed prepared in step (a) by drying the functional mixture prepared in step (b) while spraying the functional mixture through a spray nozzle of a fluid bed dryer after introducing the core seed into the fluid bed dryer;

(d) preparing a secondary coating solution by mixing 66 parts by weight of purified water, 25 parts by weight of titanium dioxide, 5 parts by weight of mica, 3 parts by weight of a hydrophobic polymer, 0.5 part by weight of cellulose gum, and 0.5 part by weight of sucrose based on 100 parts by weight of the coating solution;

(e) secondarily coating the primarily coated coating capsule of step (c) by drying the secondary coating solution prepared in step (d) while spraying the secondary coating solution through a spray nozzle of a fluid bed dryer after introducing the coating capsule into the fluid bed dryer; and (f) preparing a tertiary coating solution in which ethanol and cellulose derivatives are mixed, introducing the secondarily coated coating capsule of step (e) into a fluid bed dryer, and then drying the prepared tertiary coating solution while spraying the tertiary coating solution through a spray nozzle of the fluid bed dryer.

The present invention also provides a multi-capsule produced by the method.

The present invention also provides a cosmetic composition containing the multi-capsule as an active component. The cosmetic composition may be formulated as one or more selected from the group consisting of soft lotion, nutrition lotion, nutrition cream, massage cream, essence, eye cream, cleansing cream, cleansing foam, cleansing water, pack, spray, and powder.

In the cosmetic composition, other components in addition to the essential components in each formulation may be appropriately blended within a range which does not inhibit the purpose according to the present invention depending on the type of formulation, the purpose of use, or the like.

Further, the cosmetic composition may further contain an auxiliary typically used in the cosmetological or dermatological fields, such as a lipid material, an organic solvent, a solubilizing agent, a thickening agent, a gelating agent, an emollient, an antioxidant, a suspending agent, a stabilizer, a foaming agent, a fragrance ingredient, a surfactant, water, an ionic or nonionic emulsifying agent, a filler, a metal ion chelating agent, a chelating agent, a preservative, a blocking agent, a wetting agent, an essence oil, a dye, a pigment, a hydrophilic or lipophilic active agent, or any other components typically used in a cosmetic according to the quality or function of a final product.

However, it is preferred that the auxiliary and the mixing ratio thereof are appropriately selected so as not to affect preferred properties of the cosmetic composition according to the present invention.

The multi-capsule of the present invention may be applied in an amount of 3 to 20% based on the total content of the cosmetic composition, but the content is not limited thereto.

Hereinafter, the present invention will be described in detail with reference to Preparation Examples and Examples. However, the following Preparation Examples and Examples are only for exemplifying the present invention, and the content of the present invention is not limited by the following Preparation Examples and Examples.

Preparation Example 1: Preparation of Coating Solution

A method for preparing a coating solution for primary coating a colorant component or secondary coating a functional component for a cosmetic is as follows, and the solid content and viscosity thereof are shown in the following Table 1.

A coating solution was prepared by mixing 66 parts by weight of purified water, 25 parts by weight of titanium dioxide, 5 parts by weight of mica, 3 parts by weight of a hydrophobic polymer, 0.5 part by weight of cellulose gum, and 0.5 part by weight of sucrose based on 100 parts by weight of the coating solution.

TABLE 1

| Blending ratio and characteristics | | Ratio (%) |
|---|---|---|
| Components | Purified water | 66 |
| | Titanium dioxide | 25 |
| | Mica | 5 |
| | Hydrophobic polymer | 3 |
| | Cellulose gum | 0.5 |
| | Sucrose | 0.5 |
| Characteristics | Solid content (solid, %) | 34 |
| | Viscosity (cps) | 150 |

Blending Ratio and Characteristics of Coating Solution

Preparation Example 2: Production of Colorant Double Capsule for Cosmetic

A seed in the form of a bead was produced by introducing, into a spray dryer, a mixed solution obtained by mixing a colorant component for a cosmetic (iron oxide yellow, iron oxide red, iron oxide black, chromium oxide green, and ammonium manganese phosphate) with purified water, titanium dioxide, cellulose gum, and sucrose at the blending ratio in the following Table 2. In this case, as the spray drying conditions, the temperature of the inlet hot air was 190° C., the internal temperature of the dryer chamber was 100° C., the speed of the sprayer was 8,000 rpm, and the viscosity of the supplied solution was 500 to 700 cps.

Figure 1:
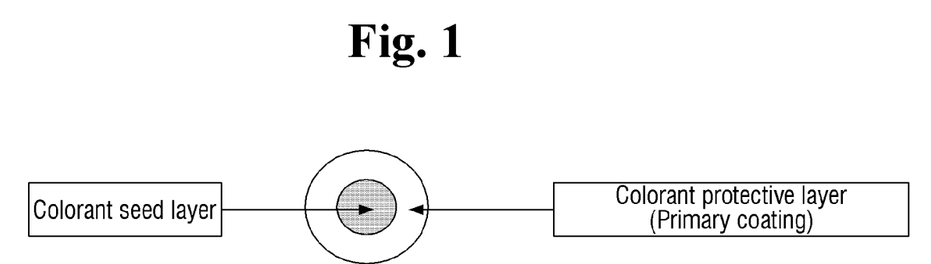
FIG. 1 illustrates a configuration of a colorant double capsule for a cosmetic of the present invention.
Figure 2:
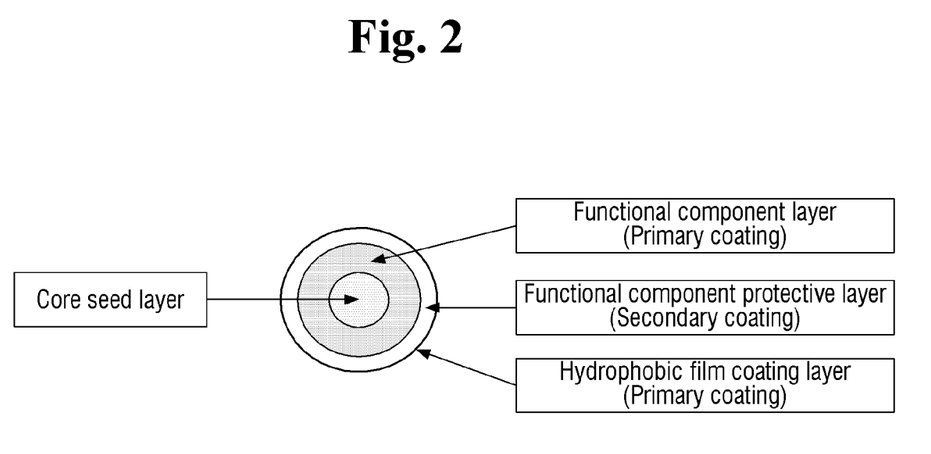
FIG. 2 illustrates a configuration of a functional multi-capsule for a cosmetic of the present invention.
Figure 3:
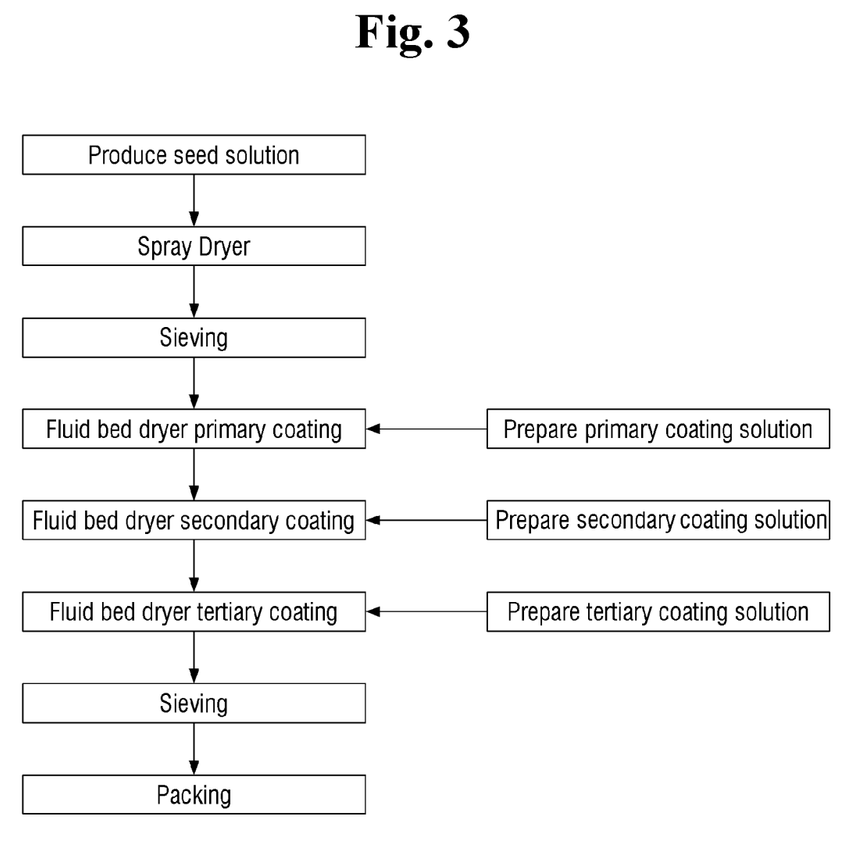
FIG. 3 is a schematic diagram of a process of producing the functional multi-capsule for a cosmetic of the present invention.
Figure 4:
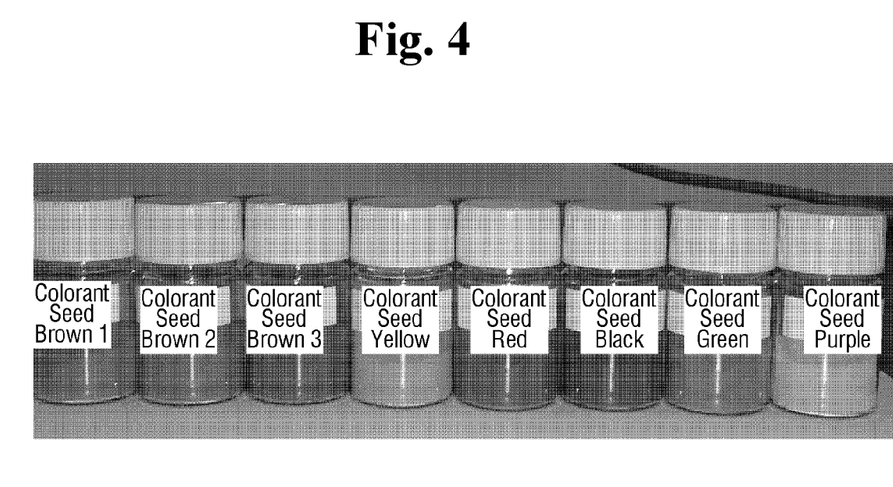
FIG. 4 is a photograph of colorant spherical seeds of the present invention.
Figure 5:
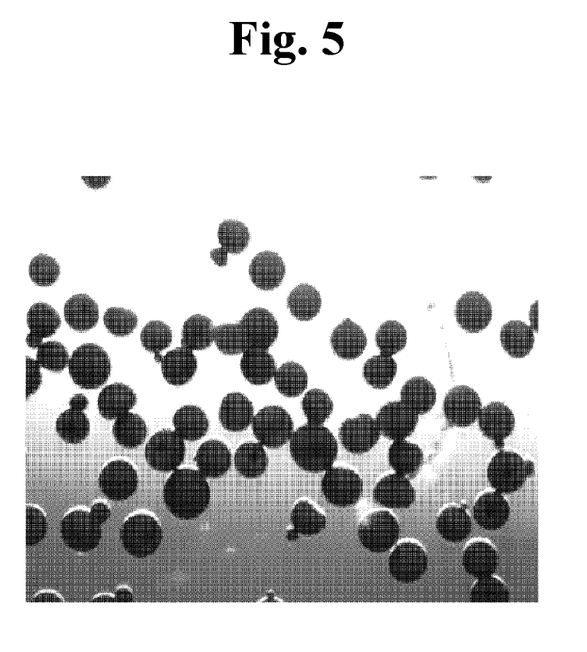
FIG. 5 is a photograph of enlarged colorant spherical seeds of the present invention.

The produced colorant component seed is as shown in FIG. 4, had a particle size of 100 to 200 μm, and exhibited a spherical bead shape when the shape was enlarged (FIG. 5). If the shape is irregular instead of the bead shape, there is a problem in that a finally desired capsule may not be manufactured because particles stick to each other during the primary capsule coating in a fluid bed dryer.

TABLE 2

Blending ratio (%) and characteristics

| | | Type of color | | | | | |
|---|---|---|---|---|---|---|---|
| | | Brown | Yellow | Red | Black | Green | Violet |
| Components | Purified water | 55 | 55 | 55 | 55 | 55 | 55 |
| | Titanium dioxide | 18.5 | 18.5 | 18.5 | 18.5 | 18.5 | 18.5 |
| | Iron oxide yellow | 15 | 25 | — | — | — | — |
| | Iron oxide red | 7 | — | 25 | — | — | — |
| | Iron oxide black | 3 | — | — | 25 | — | — |
| | Chromium oxide green | — | — | — | — | 25 | — |
| | Ammonium manganese (3+) phosphate | — | — | — | — | — | 25 |
| | Cellulose gum | 1 | 1 | 1 | 1 | 1 | 1 |
| | Sucrose | 0.5 | 0.5 | 0.5 | 0.5 | 0.5 | 0.5 |
| Characteristics | Solid content (solid, %) | 45 | 45 | 45 | 45 | 45 | 45 |
| | Viscosity (cps) | 600 | 600 | 600 | 600 | 600 | 600 |

Composition and Characteristics of Mixture for Producing Colorant Component Seed A mixture for producing a colorant component seed was produced by introducing the produced colorant seed into a fluid bed dryer and supplying the coating solution of Preparation Example 1 to dry the coating solution while spraying the coating solution onto the surface of the seed by a fluid bed bottom spray method. In this case, as the working conditions, the temperature of the inlet hot air was 90° C., the internal temperature of the product chamber was 50 to 55° C., and the viscosity of the supplied solution was 140 to 160 cps.

Figure 6:
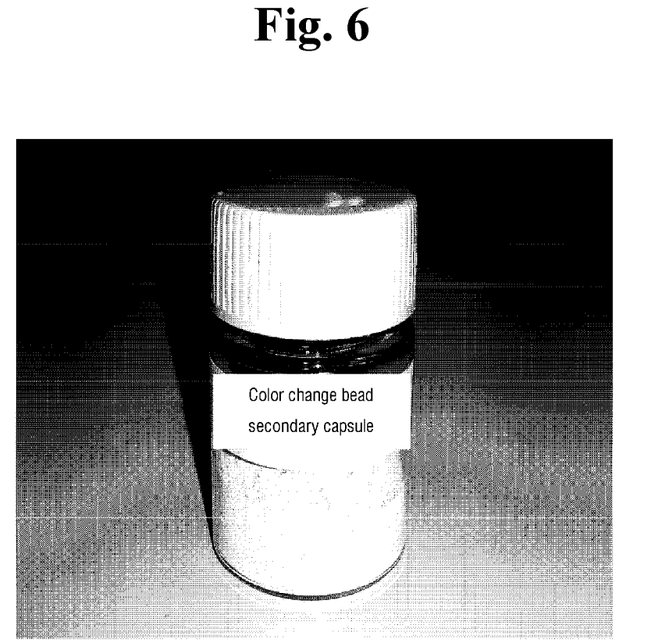
FIG. 6 is a photograph of the colorant double capsules for a cosmetic of the present invention.
Figure 7:
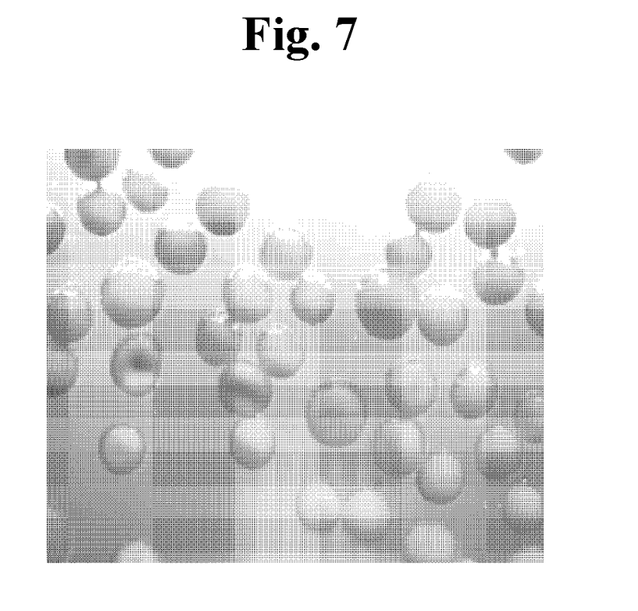
FIG. 7 is a photograph of the enlarged colorant double capsules for a cosmetic of the present invention.

The produced final colorant capsule is as shown in FIG. 6, had a particle size of 90 to 300 m, and exhibited a spherical bead shape when the shape was enlarged (FIG. 7). If the shape is irregular instead of the bead shape, there is a problem in that the capsule is easily broken in the formulation when applied to a cosmetic, and the internal colorant is easily released to the outside.

Preparation Example 3: Production of Functional Multi-Capsule for Cosmetic (1) Production of Core Seed A core seed in the form of a bead was produced by a tangential spray method by introducing the solution or powder prepared at the blending ratio in the following Table 3 into a fluid bed dryer. In this case, as the working conditions, the temperature of the inlet hot air was 80° C., the internal temperature of the dryer chamber was 55° C., and the viscosity of the supplied solution was 100 to 150 cps.

Figure 8:
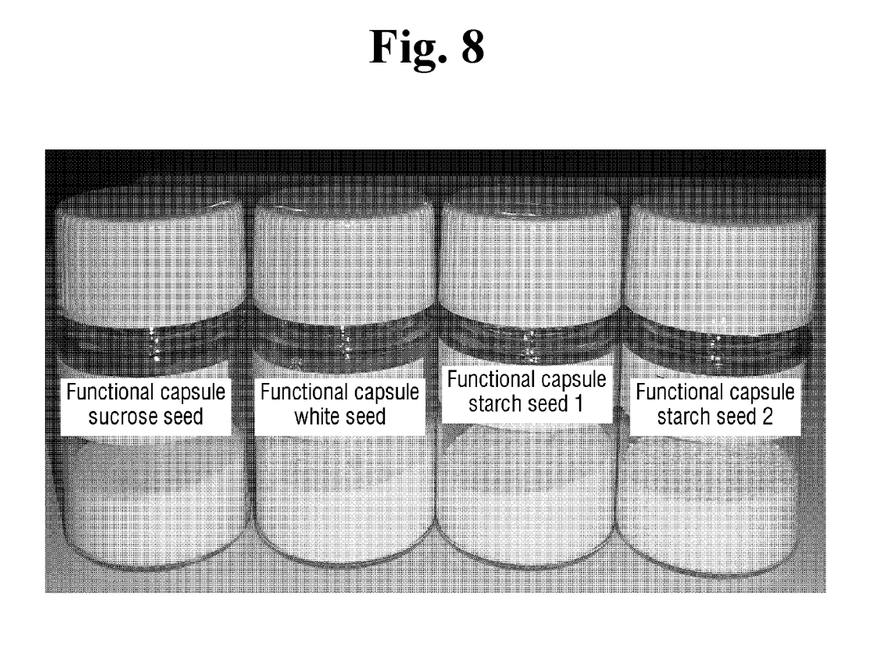
FIG. 8 is a photograph of core spherical seeds for producing a functional multi-capsule for a cosmetic of the present invention.
Figure 9:
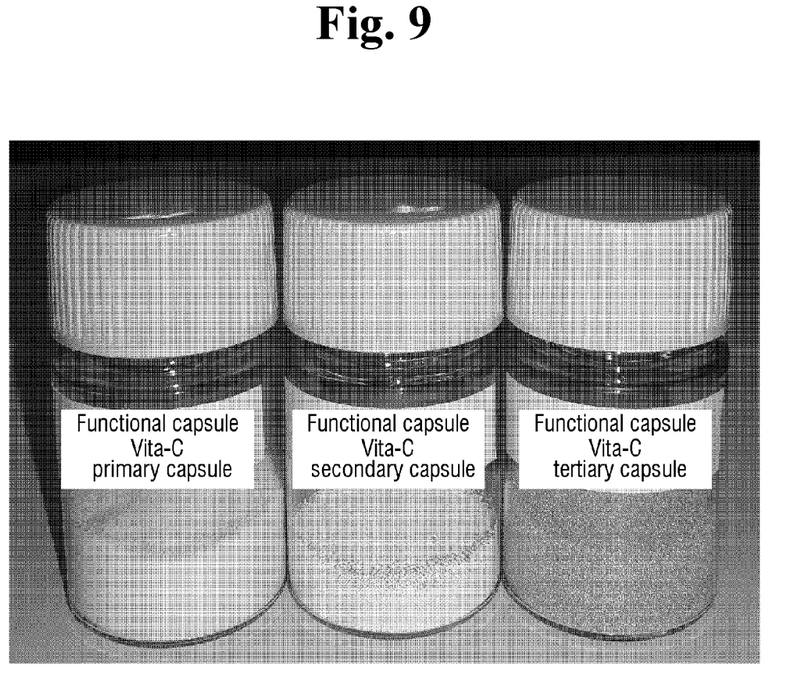
FIG. 9 is a photograph of primary coating, secondary coating, and tertiary coating capsules in the process of producing multi-capsules of cosmetic ascorbic acid functional components of the present invention.
Figure 10:
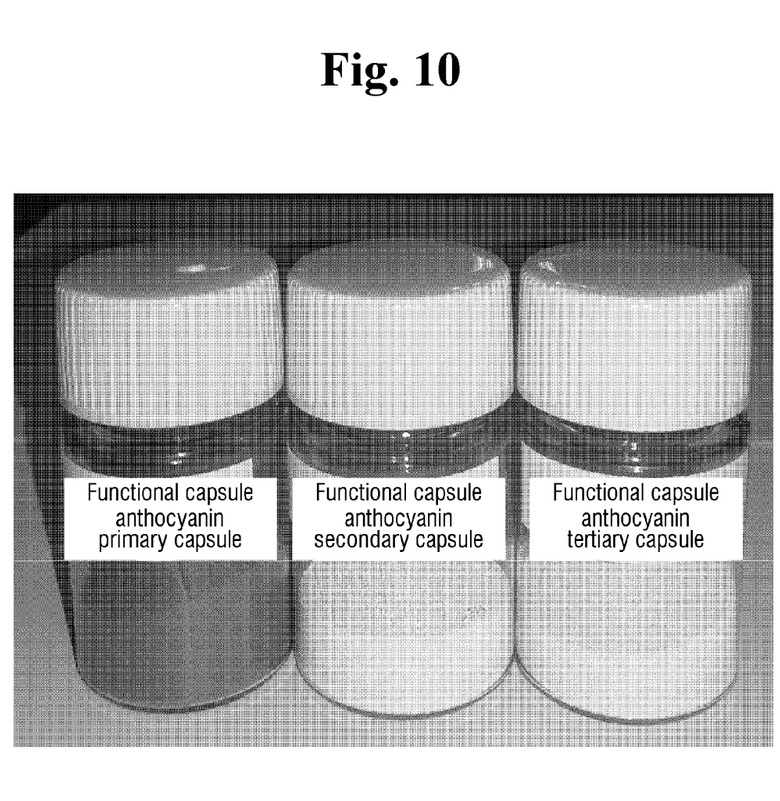
FIG. 10 is a photograph of primary coating, secondary coating, and tertiary coating capsules in the process of producing multi-capsules of cosmetic anthocyanin functional components of the present invention.

The produced core seed is as shown in FIG. 8, had a particle size of 300 to 800 jam, and was used after sorting according to the size. The shape of the particle exhibited a bead shape when observed by enlarging the particle. If the shape is irregular instead of the bead shape, there is a problem in that a finally desired capsule may not be manufactured because particles stick to each other during the primary capsule coating in a fluid bed dryer.

The produced core seeds were classified into uniform sizes by sieving and applied to the next process, and finally used selectively according to the size of the multi-capsule.

TABLE 3

| Blending ratio (%) and characteristics | | Starch seed | White seed | Sucrose seed |
|---|---|---|---|---|
| Components | Purified water | 55 | 55 | — |
| | Zea Mays Corn starch | 44 | — | — |
| | Sucrose | — | 1.5 | 100 |
| | Titanium dioxide | — | 42.5 | — |
| | Cellulose gum | 1 | 1 | — |
| Characteristics | Solid content (solid, %) | 45 | 45 | 100 |
| | Viscosity (cps) | 120 | 120 | — |

Composition and characteristics of mixture for producing core seed (2) Production of Functional Component Primary Coating Solution A functional component primary coating solution was prepared at the blending ratio in the following Table 4.

TABLE 4

Blending ratio (%) and characteristics

| | | Functional type | | | | | |
|---|---|---|---|---|---|---|---|
| | | Lycopene | Anthocyanin | Xanthophyll | Chlorophyll | Ascorbic acid | Salicylic acid |
| Components | Purified water | 66 | 66 | 66 | 66 | 66 | 66 |
| | Corn starch | 25 | 25 | 25 | 25 | 19.5 | 19.5 |
| | Lycopene | 7 | — | — | — | — | — |
| | Anthocyanin | — | 7 | — | — | — | — |
| | Xanthophyll | — | — | 7 | — | — | — |
| | Chlorophyll | — | — | — | 7 | — | — |
| | L-ascorbic acid | — | — | — | — | 12.5 | — |
| | Salicylic acid | — | — | — | — | — | 12.5 |
| | Hydrophobic polymer | 1.5 | 1.5 | 1.5 | 1.5 | 1.5 | 1.5 |
| | Cellulose gum | 0.5 | 0.5 | 0.5 | 0.5 | 0.5 | 0.5 |
| Characteristics | Solid content (solid, %) | 34 | 34 | 34 | 34 | 34 | 34 |
| | Viscosity (cps) | 100 | 100 | 100 | 100 | 100 | 100 |

Preparation of Functional Component Primary Coating Solution (3) Primary Coating Treatment A primary coating capsule was produced by introducing the produced core seed into a fluid bed dryer and supplying the functional component primary coating solution to dry a primary coating solution while spraying the primary coating solution onto the surface of the core seed powder by a fluid bed bottom spray method. In this case, as the working conditions, the temperature of the inlet hot air was 90° C., the internal temperature of the product chamber was 50 to 55° C., and the viscosity of the supplied solution was 90 to 100 cps.

(4) Secondary Coating Treatment

A secondary coating capsule was produced by supplying the coating solution prepared by the method in Preparation Example 1 to the primarily coated capsule to dry the coating solution while spraying the coating solution onto the surface of the primarily coated capsule by a fluid bed bottom spray method. In this case, as the working conditions, the temperature of the inlet hot air was 90° C., the internal temperature of the product chamber was 50 to 55° C., and the viscosity of the supplied solution was 140 to 160 cps.

(5) Preparation of Tertiary Coating Solution

A tertiary coating solution was prepared at the blending ratio in the following Table 5.

TABLE 5

| | | Blending ratio (%) and characteristics | | | | | |
|---|---|---|---|---|---|---|---|
| | | Lycopene | Anthocyanin | Xanthophyll | Chlorophyll | Ascorbic acid | Salicylic acid |
| Components | Ethanol (95%) | 98 | 98 | 98 | 98 | 88 | 98 |
| | Cellulose derivative | 2 | 2 | 2 | 2 | 2 | 2 |
| | Gold Pearl | — | — | — | — | 10 | — |
| Characteristics | Solid content (solid, %) | 2 | 2 | 2 | 2 | 12 | 2 |
| | Viscosity (cps) | 80 | 80 | 80 | 80 | 100 | 80 |

Composition and Characteristics of Tertiary Coating Solution (6) Tertiary Coating Treatment A thirdly coated multi-capsule was produced by supplying the tertiary coating solution to the secondary coating capsule to dry the tertiary coating solution while spraying the tertiary coating solution onto the surface of the secondarily coated capsule by a fluid bed bottom spray method. In this case, as the working conditions, the temperature of the inlet hot air was 40° C., the internal temperature of the product chamber was 30° C., and the viscosity of the supplied solution was 80 to 100 cps.

The produced multi-capsule may be produced in various sizes of 300 to 1,500 μm and may be produced as a capsule having various functions according to the selection of the internal functional component, and the appearance color may be also be produced as various colors desired by consumers.

Figure 11:
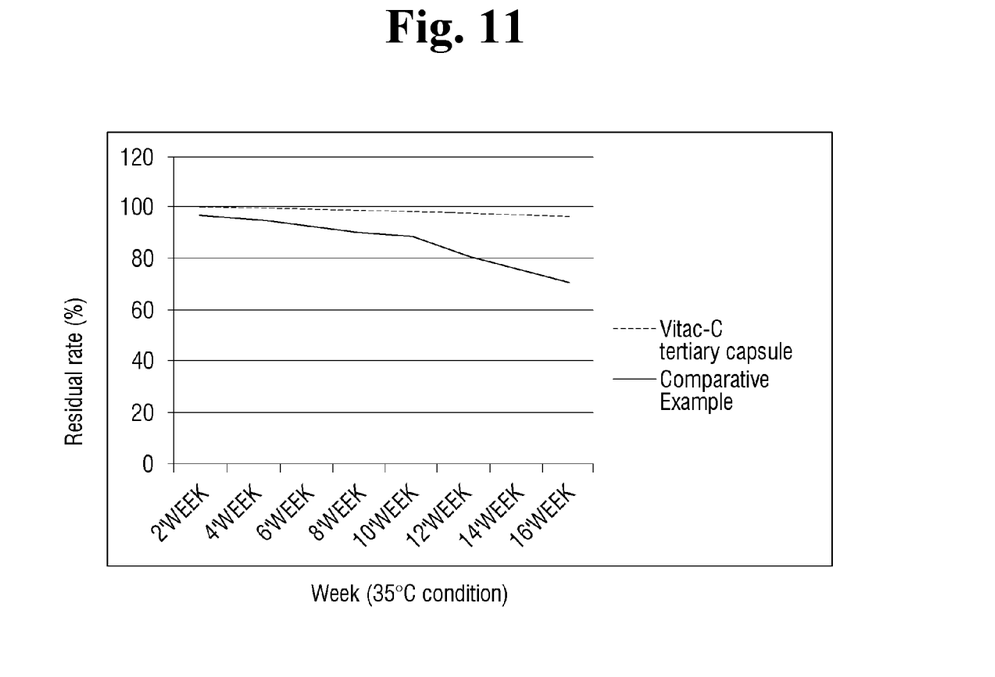
FIG. 11 is a graph comparing the ascorbic acid residual rates (%) while the ascorbic acid functional component multi-capsule of the present invention and ascorbic acid (Comparative Example) are stored at 35° C. for 16 weeks.

Example 1: Comparison of Residual Rates of Functional Multi-Capsules for Cosmetic The residual rates of the functional components were compared while the cosmetic functional multi-capsule in Preparation Example 3 was stored at 35° C. As a result of storing ascorbic acid which was not encapsulated and the ascorbic acid functional multi-capsule produced by the method in Preparation Example 3 at 35° C. for 16 weeks, it could be confirmed that the multi-encapsulated ascorbic acid multi-capsule exhibited a high ascorbic acid residual rate of 96.1% even when stored for 16 weeks, but ascorbic acid which was not encapsulated exhibited a low residual rate of 70.5% after 16 weeks (Table 6 and FIG. 11).

TABLE 6

| | Storage period | | | | | | | |
|---|---|---|---|---|---|---|---|---|
| Classification | 2 weeks | 4 weeks | 6 weeks | 8 weeks | 10 weeks | 12 weeks | 14 weeks | 16 weeks |
| Ascorbic acid multi-capsule | 99.6 | 99.1 | 98.7 | 98.3 | 97.8 | 97.5 | 96.4 | 96.1 |

TABLE 6-continued

| Classification | Storage period | | | | | | | |
|---|---|---|---|---|---|---|---|---|
| | 2 weeks | 4 weeks | 6 weeks | 8 weeks | 10 weeks | 12 weeks | 14 weeks | 16 weeks |
| Comparative Example 1 (ascorbic acid) | 97.2 | 95.3 | 92.9 | 90 | 88.4 | 81.2 | 76.3 | 70.5 |

Ascorbic Acid Residual Rate (%)

Figure 12:
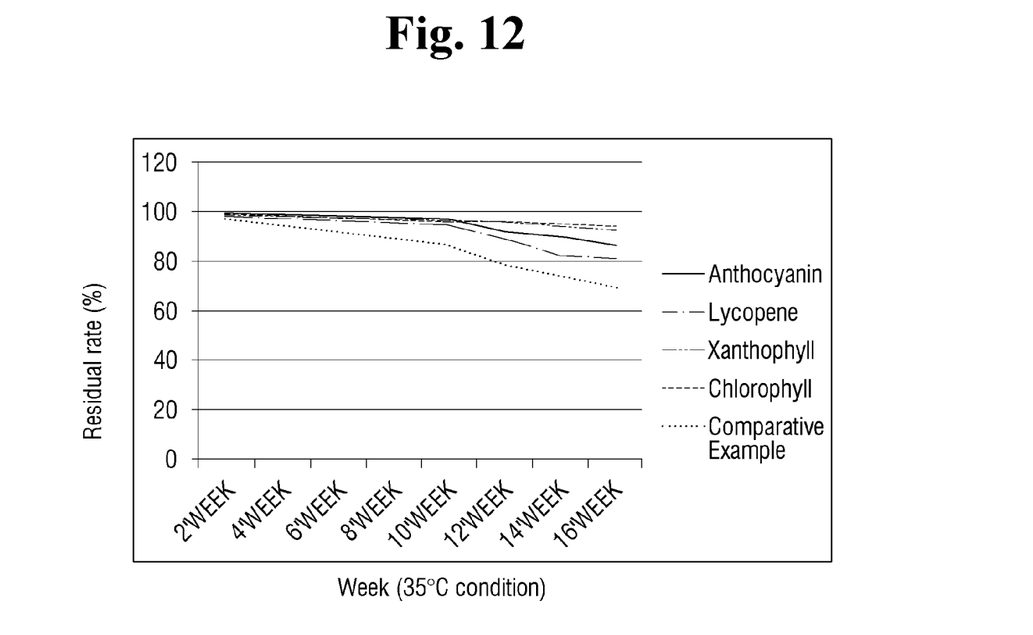
FIG. 12 is a graph comparing the respective functional component residual rates (%) while the respective functional multi-capsules of anthocyanin, lycopene, xanthophyll, and chlorophyll of the present invention and anthocyanin (Comparative Example) are stored at 35° C. for 16 weeks.

Further, as a result of also storing the respective multi-capsules of anthocyanin, lycopene, xanthophyll, and chlorophyll produced by the method in Preparation Example 3 at 35° C. for 16 weeks, all the multi-capsules exhibited a residual rate of 80% or more even after 16 weeks, but anthocyanin which was not encapsulated (Comparative Example) exhibited a low residual rate of 69.5% after 16 weeks (Table 7 and FIG. 12).

TABLE 7

| Classification | Storage period | | | | | | | |
|---|---|---|---|---|---|---|---|---|
| | 2 weeks | 4 weeks | 6 weeks | 8 weeks | 10 weeks | 12 weeks | 14 weeks | 16 weeks |
| Anthocyanin multi-capsule | 99.6 | 99 | 98.2 | 97.5 | 97.1 | 92 | 89.5 | 86.3 |
| Lycopene multi-capsule | 98.4 | 97.8 | 96.1 | 95 | 94.2 | 88.8 | 82.3 | 81 |
| Xanthophyll multi-capsule | 98.7 | 98.2 | 97.3 | 96.7 | 96.3 | 95.7 | 94.9 | 92.3 |
| Chlorophyll multi-capsule | 99.3 | 98.6 | 97.7 | 97 | 96.4 | 95.9 | 95.1 | 94 |
| Comparative Example 2 (anthocyanin) | 97.2 | 94.5 | 91.8 | 88.8 | 86.5 | 78.5 | 74.5 | 69.5 |

Functional Component Residual Rate (%)

Example 2: Comparison of Functional Component Residual Rates of Cosmetic Functional Multi-Capsules According to Blending Ratio of Coating Solution Cosmetic functional multi-capsules were produced by the method in Preparation Example 3, and the functional component residual rates were analyzed from the cosmetic functional multi-capsules coated with coating solutions prepared by varying the blending ratio of the coating solution in Preparation Example 1 used during the secondary coating (Table 8).

TABLE 8

| Components | Preparation Example 1 | Comparative Example 3 | Comparative Example 4 |
|---|---|---|---|
| Purified water | 66 | 66 | 66 |
| Titanium dioxide | 25 | 20 | 29 |
| Mica | 5 | 8 | 2 |
| Hydrophobic polymer | 3 | 4.5 | 1.5 |
| Cellulose gum | 0.5 | 1.3 | 0.2 |
| Sucrose | 0.5 | 0.2 | 1.3 |

Blending Ratio (%) of Coating Solution

As a result, it could be confirmed that during the production of the cosmetic functional multi-capsule, the production of functional multi-capsules of ascorbic acid and anthocyanin using a coating solution mixed at a blending ratio in Preparation Example 1 in the secondary coating step had a better effect of preserving the functional component than the production of the multi-capsules using the coating solutions in Comparative Examples 3 and 4 (Table 9).

TABLE 9

| Type of coating solution | | 2 weeks | 4 weeks | 6 weeks | 8 weeks | 10 weeks | 12 weeks | 14 weeks | 16 weeks |
|---|---|---|---|---|---|---|---|---|---|
| | | | | | | Storage period | | | |
| Ascorbic acid | Preparation Example 1 | 99.6 | 99.1 | 98.7 | 98.3 | 97.8 | 97.5 | 96.4 | 96.1 |
| | Comparative Example 3 | 98.2 | 97.2 | 95.4 | 91.2 | 89.2 | 85.2 | 82.4 | 78.2 |
| | Comparative Example 4 | 98.6 | 97.6 | 96.1 | 92.7 | 89.6 | 86.0 | 83.2 | 80.2 |
| Anthocyanin | Preparation Example 1 | 99.61 | 99 | 98.2 | 97.5 | 97.1 | 92 | 89.5 | 86.3 |
| | Comparative Example 3 | 97.5 | 96.2 | 94.7 | 92.4 | 90.1 | 86.7 | 82.5 | 79.8 |
| | Comparative Example 4 | 96.2 | 96.8 | 95.4 | 93.4 | 91.4 | 88.6 | 84.2 | 81.0 |

Functional Component Residual Rate (%)

Example 3: Evaluation of Feeling of Use

A cosmetic including 10% of the ascorbic acid multi-capsule produced by the method in Preparation Example 3 and an ascorbic acid multi-capsule were produced by the method in Preparation Example 3, and cosmetics including 10% of ascorbic acid multi-capsules coated with the coating solution prepared by varying the blending ratio (Table 8) of the coating solution in Preparation Example 1 used during the secondary coating were applied to the faces of total 30 adult women consisting of 10 adult women (35.4 years old on average) per treatment group twice a day for a week, and the feeling of use (spreadability, adhesiveness, residual feeling, and skin improvement effect) was evaluated by a 10-point scale method (0 point to 2 points: very poor, 2 points to 4 points: poor, 4 points to 6 points: fair, 6 points to 8 points: good, and 8 points to 10 points: very good). The residual feeling score was higher when there was less residual feeling.

TABLE 10

| Type of coating solution | Spread-ability | Adhe-siveness | Residual feeling | Skin improvement effect | Overall average |
|---|---|---|---|---|---|
| Preparation Example 1 | 7.8 | 8.2 | 8.8 | 8.0 | 8.2 |
| Comparative Example 3 | 7.2 | 7.4 | 8.0 | 7.2 | 7.45 |
| Comparative Example 4 | 7.0 | 7.3 | 7.8 | 7.3 | 7.35 |

Evaluation of Feeling of Use of Functional Component Multi-Capsules

As a result, as can be seen from Table 10, it could be seen that during the production of the multi-capsule, the production of a capsule by performing secondary coating with the coating solution in Preparation Example 1 had the best spreadability, adhesiveness, residual feeling, and skin improvement effect, and the overall average score was also 8.2 points, which indicates an excellent feeling of use.

What is claimed is:

1. A method for producing a multi-capsule, the method comprising steps of:
    (a) preparing a coating solution by mixing purified water, titanium dioxide, mica, a hydrophobic polymer, cellulose gum, and sucrose; and
    (b) drying the coating solution prepared in step (a) while spraying the coating solution through a spray nozzle of a fluid bed dryer after introducing a spherical seed of a colorant component for a cosmetic into the fluid bed dryer.

2. The method of claim 1, wherein the coating solution of step (a) is prepared by mixing 63 to 69 parts by weight of purified water, 23 to 27 parts by weight of titanium dioxide, 4 to 6 parts by weight of mica, 2.5 to 3.5 parts by weight of a hydrophobic polymer, 0.4 to 0.6 part by weight of cellulose gum, and 0.4 to 0.6 part by weight of sucrose based on 100 parts by weight of the coating solution.

3. The method of claim 2, wherein the method of producing the multi-capsule comprises steps of:
    (a) preparing a seed of a colorant component by spray-drying a mixture obtained by mixing a colorant component for a cosmetic selected from the group consisting of iron oxide yellow, iron oxide red, iron oxide black, chromium oxide green, and ammonium manganese phosphate with purified water, titanium oxide, cellulose gum, and sucrose;
    (b) preparing a coating solution by mixing 63 to 69 parts by weight of purified water, 23 to 27 parts by weight of titanium dioxide, 4 to 6 parts by weight of mica, 2.5 to 3.5 parts by weight of a hydrophobic polymer, 0.4 to 0.6 part by weight of cellulose gum, and 0.4 to 0.6 part by weight of sucrose based on 100 parts by weight of the coating solution; and
    (c) drying the coating solution prepared in step (b) while spraying the coating solution through a spray nozzle of a fluid bed dryer after introducing the seed of the colorant component prepared in step (a) into the fluid bed dryer.

4. A multi-capsule produced by the method of claim 1.

5. A cosmetic composition comprising the multi-capsule of claim 4 as an active component.

* * * * *